(12) United States Patent
Ceradini

(10) Patent No.: US 9,943,398 B2
(45) Date of Patent: Apr. 17, 2018

(54) INCREASING SURVIVAL OF FREE TISSUE GRAFTS AND FLAPS USING PHOSPHODIESTERASE TYPE 5 (PDE5) INHIBITORS

(71) Applicant: New York University, New York, NY (US)

(72) Inventor: Daniel J. Ceradini, Howard Beach, NY (US)

(73) Assignee: New York University, New York, NY (US)

( * ) Notice: Subject to any disclaimer, the term of this patent is extended or adjusted under 35 U.S.C. 154(b) by 454 days.

(21) Appl. No.: 13/943,538

(22) Filed: Jul. 16, 2013

(65) Prior Publication Data

US 2014/0018936 A1    Jan. 16, 2014

Related U.S. Application Data

(60) Provisional application No. 61/672,176, filed on Jul. 16, 2012.

(51) Int. Cl.
| | | |
|---|---|---|
| *A61K 31/519* | (2006.01) | |
| *A61K 31/53* | (2006.01) | |
| *A61K 31/513* | (2006.01) | |
| *A61F 2/02* | (2006.01) | |
| *A61L 27/36* | (2006.01) | |
| *A61L 27/50* | (2006.01) | |
| *A61L 27/54* | (2006.01) | |

(52) U.S. Cl.
CPC ............. *A61F 2/02* (2013.01); *A61L 27/362* (2013.01); *A61L 27/3604* (2013.01); *A61L 27/3608* (2013.01); *A61L 27/3612* (2013.01); *A61L 27/3625* (2013.01); *A61L 27/3687* (2013.01); *A61L 27/507* (2013.01); *A61L 27/54* (2013.01); *A61L 2300/434* (2013.01); *A61L 2400/06* (2013.01)

(58) Field of Classification Search
CPC .... C07D 487/04; A61K 31/519; A61K 31/53; A61K 31/513
See application file for complete search history.

(56) References Cited

U.S. PATENT DOCUMENTS 7,091,207 B2 *   8/2006   Kukreja ................. A61K 31/00
                                                        514/234.5

OTHER PUBLICATIONS

Gori et al. (Circulation, 2005, 111(6), pp. 742-746).*
Satterfiled et al. (J. Nutr., 2010, 140(2), abstract).*
Senthilkumar et al. (Arteriosclerosis, Thrombosis, and Vascular Biology. 2007;27:1947-1954).*
U.S. Food and Drug Administration (Route of Administration, http://www.fda.gov/Drugs/DevelopmentApprovalProcess/Forms-SubmissionRequirements/ElectronicSubmissions/DataStandardsManualmonographs/ucm071667.htm, downloaded Sep. 30, 2016).*
Choi et. al. (Am. J. Physiol. Renal Physiol., 2009, 297, pp. F362-F370).*
Flores et al., "Saphenous Vein Grafts for Perforator Flap Salvage in Autologous Breast Reconstruction," Microsurgery 29:236-239 (2009).
Hart et al., "Short- and Long-Term Effects of Sildenafil on Skin Flap Survival in Rats," Laryngoscope 116:522-528 (2006).
Korom et al., "Sildenafil Extends Survival and Graft Function in a Large Animal Lung Transplantation Model," Eur. J. Cardiothorac. Surg. 29:288-293 (2006).
Rad et al., "Clinical Experience With the Lateral Septocutaneous Superior Gluteal Artery Perforator Flap for Autologous Breast Reconstruction," Microsurgery 30:339-347 (2010).
Sarifakioglu et al., "The Influence of Sildenafil on Random Skin Flap Survival in Rats: An Experimental Study," Br. J. Plast. Surg. 57:769-772 (2004).
Tsai et al., "Evaluation of the Effect of Sildenafil and Vascular Endothelium Growth Factor Combination Treatment on Skin Flap Survival in Rats," Aesth. Plast. Surg. 32:624-631 (2008).
Ulusoy et al., "Improved Flap Viability With Site-Specific Delivery of Sildenafil Citrate Using Fibrin Glue," Ann. Plast. Surg. 55(3):292-296 (2005).

* cited by examiner

*Primary Examiner* — Susanna Moore
(74) *Attorney, Agent, or Firm* — LeClairRyan PLLC

(57) ABSTRACT

The present invention relates to methods of tissue grafting and microvascular free flap transfer that involve administering a phosphodiesterase type-5 inhibitor to the tissue graft or microvascular free flap to produce a treated graft or flap, and implanting the treated graft or flap into a recipient site of a host subject.

8 Claims, 5 Drawing Sheets

A.

B.

**p<0.01

INCREASING SURVIVAL OF FREE TISSUE GRAFTS AND FLAPS USING PHOSPHODIESTERASE TYPE 5 (PDE5) INHIBITORS

This application claims the priority benefit of U.S. Provisional Patent Application Ser. No. 61/672,176, filed Jul. 16, 2012, which is hereby incorporated by reference in its entirety

FIELD OF THE INVENTION

The present invention relates to the use of phosphodiesterase-5 inhibitors to prolong the survival of free tissue grafts and flaps following transfer.

BACKGROUND OF THE INVENTION

Autologous fat has been used as a filler material to correct soft tissue defects of various sizes for over 100 years. It was first introduced by Neuber to the German Surgical Society in 1893 and used for purposes of soft tissue augmentation in 1911. The advent of liposuction techniques in the 1980's simplified harvest and led to widespread clinical utility. Its applications range from reconstructive treatments such as augmentation of paralyzed vocal cords, repair of spinal dura and facial reconstructions in HIV patients, to cosmetic enhancements, such as breast augmentation and hand/face rejuvenation. Compared with collagen, hyaluronic acid, silicone and other filler materials on the market, autologous fat grafts offer the advantages of low cost, availability in most patients, no immunogenicity, allergenicity, or potential for transmitting infectious diseases. However, because of the unpredictable behavior of the graft, clinicians are faced with uncertainty concerning the ultimate volume maintenance of the graft at its recipient site. Transplanted adipose tissue can quickly be resorbed and replaced by fibrous tissue and cysts. Necrosis of the graft as a result of poor vascularization is also another limiting factor. To date long-term graft retention has been highly variable, varying from disappointing to lasting many years, making it difficult to predict outcome. These issues have limited the widespread adoption of autologous fat as the ideal soft tissue filler. It is now widely accepted that the adequacy of graft perfusion is considered key to its fate after transplantation.

Over 50,000 autologous fat grafting procedures were performed in 2010, with a total predicted revenue approaching 98 million dollars. Thus, improving the predictability and long-term survival of autologous fat grafts would have an enormous clinical impact in the field of reconstructive plastic surgery. The present invention is directed to overcoming these and other deficiencies in the art.

SUMMARY OF THE INVENTION

A first aspect of the present invention relates to a method of tissue grafting. This method involves administering a phosphodiesterase type-5 (PDE5) inhibitor to a tissue graft to produce a treated tissue graft, and implanting the treated tissue graft into a recipient site of a host subject after said administering.

Another aspect of the present invention relates to an isolated tissue graft treated with a phosphodiesterase type-5 (PDE5) inhibitor.

Another aspect of the present invention relates to a method of microvascular free flap transfer. This method involves administering a phosphodiesterase type-5 (PDE5) inhibitor to a microvascular free flap to produce a treated microvascular free flap, and implanting the treated microvascular free flap into a recipient site of a host subject after said administering.

Tissue grafts and microvascular free flaps have been utilized for centuries by surgeons for reconstruction of soft tissue/bone defects, revascularization of the heart and limbs, organ transplantation, autologous fat grafting, etc. One unsolved clinical problem in many of these surgical procedures is the unreliability and unpredictability of tissue survival following grafting. The clinical problem of tissue graft or microvascular free flap "take", i.e., survival after being transplanted from one part of the body to another, has been around for centuries. Surprisingly, there have been virtually no rationally designed or translated therapeutics to improve graft take. As described herein, phosphodiesterase-5 (PDE5) inhibitors are FDA approved compounds that when utilized to pre-treat grafts and flaps before they are harvested "protect" them from necrosis following re-implantation or inset. As demonstrated herein, pretreatment with PDE-5 inhibitors makes the graft/flap take more efficient, predictable, and reliable.

BRIEF DESCRIPTION OF THE DRAWINGS

FIG. 3A is a graph showing the time course of vascular flux in the saline treated ("control"; -■-) or sildenafil treated ("PDE5i-protected"; -●-) grafts after explantation. A significant improvement in revascularization within the core of the sildenafil-treated graft as compared to control was observed at 1 and 2 weeks post grafting. FIG. 3B is a Doppler analysis of vascular flux in control saline treated (top images) and sildenafil-treated (bottom images) grafts at 2 weeks post grafting.

FIG. 4A is a panel of photographic images showing the effect of sildenafil treatment on graft tissue volume after transfer. Compared to the saline treated graft, which is resorbed quickly over the course of 12-weeks following transfer (FIG. 4A; bottom row of images), the sildenafil treated graft maintained virtually all of its volume over time (FIG. 4A; top row of images). FIG. 4B is a graft survival analysis comparing the long term survival of sildenafil treated grafts ("PDE5I-protected) with saline treated grafts ("control") and devascularized grafts (trypsin-inactivated).

FIG. 5A is a graph showing graft weight retention of explanted grafts at 2 and 8 weeks post grafting. FIG. 5B is a volumetric analysis of control (left) and sildenafil treated (right) grafts via an in situ 3-D ultrasound rendering at 8 weeks post grafting.

DETAILED DESCRIPTION OF THE INVENTION

Figures 1A, 1B:
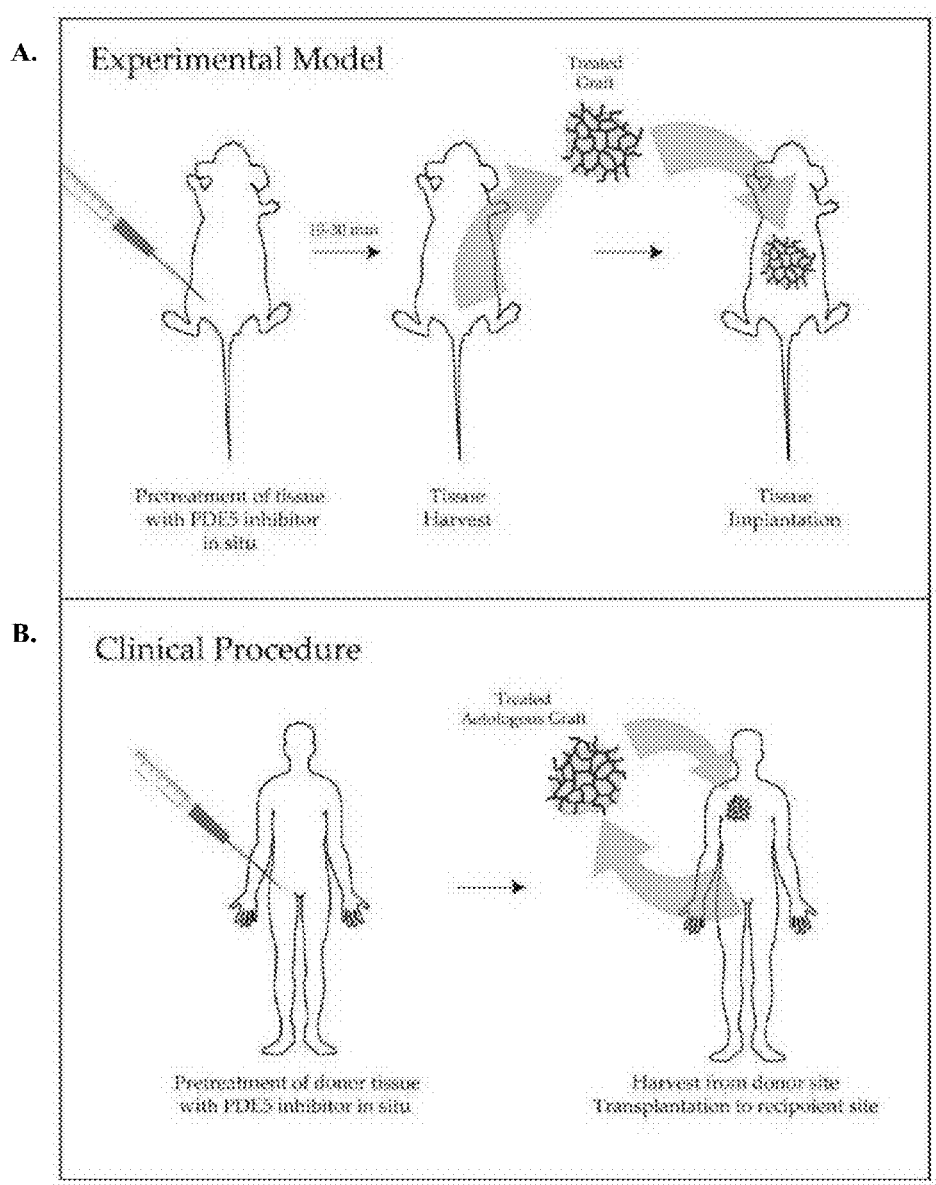
FIGS. 1A-1B are schematic representations of the tissue grafting procedure of the present invention involving the pretreatment of the tissue graft with a PDE-5 inhibitor prior to harvest and transfer in an experimental animal model (FIG. 1A) and in clinical use (FIG. 1B).

A first aspect of the present invention relates to a method of tissue grafting. This method involves administering a phosphodiesterase type-5 (PDE5) inhibitor to a tissue graft to produce a treated tissue graft, and implanting the treated tissue graft into a recipient site of a host subject after said administering.

In accordance with this aspect of the invention "tissue grafting" refers to a surgical procedure involving the transfer of tissue from one site (i.e., a donor site) on an individual's body to another site on the same individual's body or to another site on a different individual's body (i.e., a recipient site). The tissue graft comprises one or more tissue or cell types, but does not comprise a whole, internal organ (i.e., tissue grafting does not encompass transfer of a whole internal organ). While a tissue graft may contain blood vessels, it does not contain an intact microcirculatory system. Therefore, the tissue graft is not surgically reattached to the recipient circulatory system to survive. Rather, the tissue graft relies on the blood supply at the recipient site for survival.

The tissue graft may be autologous to the recipient host (i.e., obtained from the recipient), allogeneic to the recipient host (i.e., obtained from a donor subject other than the recipient), or xenogenic to the recipient host (i.e., obtained from a different species, e.g., a non-human donor, such as, for example, a pig). For allogeneic sources, the closest possible immunological match between donor and recipient is desired. If an autologous source is not available or warranted, donor and recipient Class I and Class II histocompatibility antigens can be analyzed to determine the closest match available. This minimizes or eliminates immune rejection and reduces the need for immunosuppressive or immunomodulatory therapy. If required, immunosuppressive or immunomodulatory therapy can be started before, during, and/or after the graft is introduced into a patient. For example, cyclosporin A, or other immunosuppressive drugs, can be administered to the recipient. In exemplary embodiments, autologous grafts are used.

In accordance with this and other aspects of the present invention, suitable subjects, i.e., donor and host subjects of the tissue grafting procedure described herein, include any vertebrate animals, most typically a mammal, such as a human or a non-human mammal.

Any type of tissue graft can be treated in accordance with the methods of the present invention. Typical kinds of tissue grafts include, without limitation, fat tissue, skin, muscle, bone, nerve cartilage, tendon, and blood vessels or vasculature grafts.

In one embodiment of the present invention, the tissue graft is an autologous fat graft. Autologous fat grafting is a widely utilized technique for reconstruction as well as aesthetic improvement. This procedure involves harvesting fat (i.e., adipose tissue) from one part of an individual's body and injecting it into another part of the individual's body to provide soft tissue filler that is autologous, elicits minimal immune response, and is potentially permanent. Reconstructive uses of fat tissue grafts or transfers include, without limitation, reconstruction after cancer or tumor removal (e.g., breast reconstruction after mastectomy), facial reconstruction, (e.g., congenital facial deformities, traumatic deformities of the face, post-ablative facial deformities, Perry-Rhomberg disease, and HIV-lipodystrophy), treatment of radiation damage to skin (e.g., following radiation for breast cancer), and treatment of burns. Aesthetic or cosmetic uses of fat transfers or grafts include, without limitation, rejuvenation of an aging face, rejuvenation of aging hands, lip augmentation, buttock augmentation, breast augmentation, correction of breast asymmetry, correction of lipodystrophy, and the like. Any type of fat tissue may be utilized, including subcutaneous depots from such areas as the chest, abdomen and buttocks, hips and waist. Visceral fat depots may also be used, such as that found above the kidneys.

In another embodiment of the present invention, the tissue graft is a muscle tissue graft. In accordance with this embodiment, the tissue graft may comprise skeletal muscle, cardiac muscle, or smooth muscle. Methods and compositions for muscle tissue grafts are described in U.S. Pat. No. 7,001,430 to Mills et al., U.S. Pat No. 7,131,994 to Mills et al., which are hereby incorporated by reference in their entirety.

In one embodiment of the present invention, the tissue graft comprises skeletal muscle. Skeletal muscle tissue from any appropriate source in the body is suitable for use in the methods of the present invention. Exemplary sources of skeletal muscle tissue include the back, neck, and chest, including the pectoralis major, rectus abdominis, diaphragm, trapezius, and latissimus dorsi; the shoulder and arm, including the deltoid, triceps brachii, and biceps brachii; and the leg and ankle, including the gluteus maximus, sartorius, quadriceps femoris, gracilis, hamstrings, biceps femoris, semitendinosus, gastrocnemius, and achilles tendon. In exemplary embodiments, muscle tissue is obtained from a source that is easily accessible, which minimizes the invasiveness of the procedure to obtain the tissue, and which minimizes the injury to the site from which the tissue was obtained. Exemplary muscle tissue sources include muscles of the thigh, calf, bicep and forearm. Like fat tissue grafting, muscle grafting can be utilized for both reconstructive purposes, e.g., myocardial repair, peripheral nerve repair, and repair of muscular tissue after cancer removal, as well as aesthetic and cosmetic improvements.

In another embodiment of the present invention, the tissue graft is a bone tissue graft. Suitable autologous bone tissue for grafting can be harvested from non-essential bones such as the iliac crest, fibula, ribs, mandible, and some parts of the skull. A suitable autograft can also comprise a non-solid bony structure, such as bone reamed from the anterior superior iliac spine. Allograft bone transfers using bone harvested from cadavers are also commonly performed. Bone tissue from a cadaver can be harvested from any bone. There are a variety of clinical uses for bone grafts including, without limitation, augmenting bony fusions, aiding in the repair of fractures, filling or bridging bone defects, assisting in the attachment of prosthetic devices, and treatment of periodontal disease or other dental repair processes.

In another embodiment of the present invention, the tissue graft is a composite tissue graft, i.e., composed of bone and skin, muscle and skin, adipose tissue and skin, fascia and muscle, or other such combination known to normally be present in the vertebrate body.

Tissue may be harvested from a subject using methods standard in the art for obtaining tissue for grafting. For example, such tissue may be surgically extracted using standard or minimally invasive surgical techniques. Minimal-invasive surgery (MIS) refers to surgical procedures using surgical and diagnostic instruments specially developed to reduce the amount of physical trauma associated with the procedure. Generally, MIS involves instruments that may be passed through natural or surgically created openings of small diameter into a body to a desired location of use so that surgical intervention is possible with substantially less stress being imposed on the patient, for example, without general anesthesia. MIS may be accomplished using visualization methods such as fiberoptic or microscopic means. Examples of MIS include, for example, arthoscopic surgery, laparoscopic surgery, and endoscopic surgery.

Suitable PDE5 inhibitors for use in this and all aspects of the present invention are well known in the art. In one embodiment of the present invention the PDE5 inhibitor is a pyrazolo[4,3-d]pyrimidin-7-ones as disclosed in U.S. Pat. No. 6,469,012 to Ellis and Terrett, which is hereby incorporated by reference in its entirety. Suitable PDE5 inhibitors of this kind comprise a formula of Formula I:

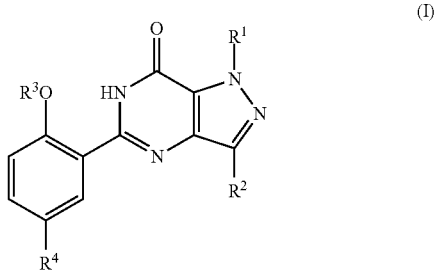

(I)

wherein $R^1$ of Formula I is H; $C_1$-$C_3$ alkyl; $C_1$-$C_3$ perfluoroalkyl; or $C_3$-$C_5$ cycloalkyl;

$R^2$ of Formula I is H; $C_1$-$C_6$ alkyl optionally substituted with $C_3$-$C_6$ cycloalkyl; $C_1$-$C_3$ perfluoroalkyl; or $C_3$-$C_6$ cycloalkyl;

$R^3$ of Formula I is $C_1$-$C_6$ alkyl optionally substituted with $C_3$-$C_6$ cycloalkyl; $C_1$-$C_6$ perfluoroalkyl; $C_3$-$C_5$ cycloalkyl; $C_3$-$C_6$ alkenyl; or $C_3$-$C_6$ alkynyl;

$R^4$ of Formula I is $C_1$-$C_4$ alkyl optionally substituted with OH, $NR^5R^6$, CN, $CONR^5R^6$ or $CO_2R^7$; $C_2$-$C_4$ alkenyl optionally substituted with CN, $CONR^5R^6$ or $CO_2R^7$; $C_2$-$C_4$ alkanoyl optionally substituted with $NR^5R^6$; (hydroxy)$C_2$-$C_4$ alkyl optionally substituted with $NR^5R^6$; ($C_2$-$C_3$ alkoxy)$C_1$-$C_2$ alkyl optionally substituted with OH or $NR^5R^6$; $CONR^5R^6$; $CO_2R^7$; halo; $NR^5R^6$; $NHSO_2NR^5R^6$; $NHSO_2R^8$; $SO_2NR^9R^{10}$; or phenyl, pyridyl, pyrimidinyl, imidazolyl, oxazolyl, thiazolyl, thienyl or triazolyl any of which is optionally substituted with methyl;

$R^5$ and $R^6$ of Formula I are each independently H or $C_1$-$C_4$ alkyl, or together with the nitrogen atom to which they are attached form a pyrrolidinyl, piperidino, morpholino, 4-N($R^{11}$)-piperazinyl or imidazolyl group wherein said group is optionally substituted with methyl or OH;

$R^7$ of Formula I is H or $C_1$-$C_4$ alkyl;

$R^8$ of Formula I is $C_1$-$C_3$ alkyl optionally substituted with $NR^5R^6$;

$R^9$ and $R^{10}$ of Formula I together with the nitrogen atom to which they are attached form a pyrrolidinyl, piperidino, morpholino or 4-N($R^{12}$)-piperazinyl group wherein said group is optionally substituted with $C_1$-$C_4$ alkyl, $C_1$-$C_3$ alkoxy, $NR^{13}R^{14}$ or $CONR^{13}R^{14}$;

$R^{11}$ of Formula I is H; $C_1$-$C_3$ alkyl optionally substituted with phenyl; (hydroxy)$C_2$-$C_3$ alkyl; or $C_1$-$C_4$ alkanoyl;

$R^{12}$ of Formula I is H; $C_1$-$C_6$ alkyl; ($C_1$-$C_3$ alkoxy)$C_2$-$C_6$ alkyl; (hydroxy)$C_2$-$C_6$ alkyl; ($R^{13}R^{14}$N)$C_2$-$C_6$ alkyl; ($R^{13}R^{14}$NOC)$C_1$-$C_6$ alkyl; $CONR^{13}R^{14}$; $CSNR^{13}R^{14}$; or $C(NH)NR^{13}R^{14}$; and $R^{13}$ and $R^{14}$ of Formula I are each independently H; $C_1$-$C_4$ alkyl; ($C_1$-$C_3$ alkoxy)$C_2$-$C_4$ alkyl; or (hydroxy)$C_2$-$C_4$ alkyl;

or a pharmaceutically acceptable salt thereof, or a pharmaceutical composition containing either entity.

In the above definition, unless otherwise indicated, alkyl groups having three or more carbon atoms, alkenyl and alkynyl groups having four or more carbon atoms, alkoxy groups having three carbon atoms and alkanoyl groups having four carbon atoms may be straight chain or branched chain. Halo means fluoro, chloro, bromo or iodo.

The compounds of Formula I may contain one or more asymmetric centres and thus they can exist as enantiomers or diastereoisomers. Furthermore, certain compounds of Formula I which contain alkenyl groups may exist as cis-isomers or trans-isomers. In each instance, the invention includes both mixtures and separate individual isomers. The compounds of Formula I may also exist in tautomeric forms and the invention includes both mixtures and separate individual tautomers.

Pharmaceutically acceptable salts of the compounds of Formula I contain a basic centre are, for example, non-toxic acid addition salts formed with inorganic acids such as hydrochloric, hydrobromic, sulphuric and phosphoric acid, with organo-carboxylic acids, or with organo-sulphonic acids. Compounds of Formula I can also provide pharmaceutically acceptable metal salts, in particular non-toxic alkali metal salts, with bases. Examples include the sodium and potassium salts.

A preferred pyrazolopyrimidinone PDE5 inhibitor of Formula I the present invention comprises sildenafil (available under the tradename Viagra® from Pfizer, Inc., New York, N.Y.) having the formula of Formula II:

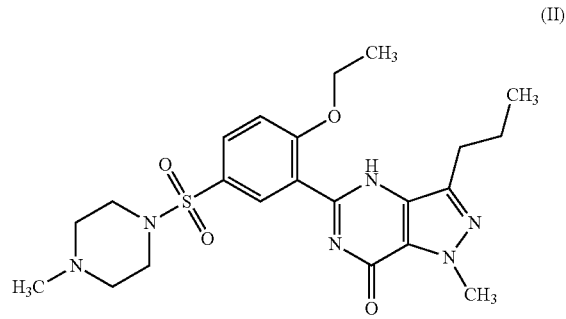 [SMILES: CCCc1nn(C)c2c(=O)nc(-c3cc(S(=O)(=O)N4CCN(C)CC4)ccc3OCC)[nH]c12]

(II)

Preferably, the PDE5 inhibitor is sildenafil citrate, i.e., 5-{2-Ethoxy-5-[(4-methyl-1-piperazinyl)sulfonyl]phenyl}-1-methyl-3-propyl-1,4-dihydro-7H-pyrazolo[4,3-d]pyrimidin-7-one 2-hydroxy-1,2,3-propanetricarboxylate (1:1).

Other suitable PDE5 inhibitors of Formula I that can be utilized in the methods of the present invention are disclosed in U.S. Pat. No. 6,469,012 to Ellis and Terrett, which is hereby incorporated by reference in its entirety, and include, without limitation:

5-(2-ethoxy-5-morpholinoacetylphenyl)-1-methyl-3-n-propyl-1,6-dihydro-7H-pyrazolo[4,3-d]pyrimidin-7-one;

5-(5-morpholinoacetyl-2-n-propoxyphenyl)-1-methyl-3-n-propyl-1,6-dihydro-7H-pyrazolo[4,3-d]pyrimidin-7-one;

5-[2-ethoxy-5-(4-methyl-1-piperazinylsulphonyl)-phenyl]-1-methyl-3-n-propyl-1,6-dihydro-7H-pyrazolo[4,3-d]pyrimidin-7-one;

5-[2-allyloxy-5-(4-methyl-1-piperazinylsulphonyl)-phenyl]-1-methyl-3-n-propyl-1,6-dihydro-7H-pyrazolo[4,3-d]pyrimidin-7-one;

5-{2-ethoxy-5-[4-(2-propyl)-1-piperazinyl-sulphonyl]phenyl}-1-methyl-3-n-propyl-1,6-dihydro-7H-pyrazolo[4,3-d]pyrimidin-7-one;

5-{2-ethoxy-5-[4-(2-hydroxyethyl)-1-piperazinyl-sulphonyl]phenyl}-1-methyl-3-n-propyl-1,6-dihydro-7H-pyrazolo[4,3-d]pyrimidin-7-one;

5-{5-[4-(2-hydroxyethyl)-1-piperazinylsulphonyl]-2-n-propoxyphenyl}-1-methyl-3-n-propyl-1,6-dihydro-7H-pyrazolo[4,3-d]pyrimidin-7-one;

5-[2-ethoxy-5-(4-methyl-1-piperazinylcarbonyl)-phenyl]-1-methyl-3-n-propyl-1,6-dihydro-7H-pyrazolo[4,3-d]pyrimidin-7-one; and 5-[2-ethoxy-5-(1-methyl-2-imidazolyl)phenyl]-1-methyl-3-n-propyl-1,6-dihydro-7H-pyrazolo[4,3-d]pyrimidin-7-one.

In another embodiment of the present invention, the PDE5 inhibitor is a tetracyclic derivative as disclosed in U.S. Pat. No. 6,140,329 to Daugan, which is hereby incorporated by reference in its entirety. Suitable PDE5 inhibitors of this kind comprise a formula of Formula III:

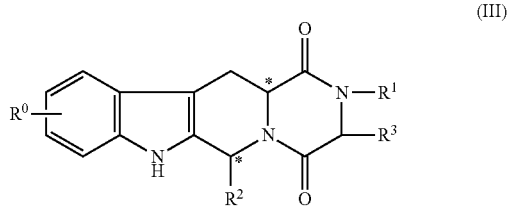

(III)

and salts and solvates thereof, in which:
  $R^0$ of Formula III represents hydrogen, halogen or $C_1$-$C_6$ alkyl;
  $R^1$ of Formula III represents hydrogen, $C_1$-$C_6$ alkyl, $C_2$-$C_6$ alkenyl, $C_2$-$C_6$ alkynyl, halo$C_1$-$C_6$ alkyl, $C_3$-$C_8$cycloalkyl, $C_3$-$C_8$cycloalkyl-$C_1$-$C_3$ alkyl, aryl $C_1$-$C_3$alkyl or heteroaryl $C_1$-$C_3$alkyl;
  $R^2$ of Formula III represents an optionally substituted mono-cyclic aromatic ring selected from benzene, thiophene, furan and pyridine or an optionally substituted bicyclic ring

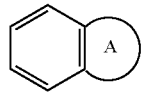

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and
  $R^3$ of Formula III represents hydrogen or $C_1$-$C_3$alkyl, or $R^1$ and $R^3$ together represent a 3- or 4-membered alkyl or alkenyl chain.

The pharmaceutically acceptable salts of the compounds of Formula III are acid addition salts formed with pharmaceutically acceptable acids. Examples include the hydrochloride, hydrobromide, sulphate or bisulphate, phosphate or hydrogen phosphate, acetate, benzoate, succinate, fumarate, maleate, lactate, citrate, tartrate, gluconate, methanesulphonate, benzenesulphonate and p-toluenesulphonate salts.

Compounds of Formula III can also provide pharmaceutically acceptable metal salts, in particular alkali metal salts, with bases. Examples include the sodium and potassium salts. Other suitable compounds of Formula III and methods of making the same are disclosed in U.S. Pat. No. 6,140,329 to Daugan, which is hereby incorporated by reference in its entirety.

A preferred PDE5 inhibitor of Formula III comprises tadalafil (available under the tradename Cialis® from Lilly ICOS LLC; Indianapolis, Ind.). Tadafil has a formula of Formula IV:

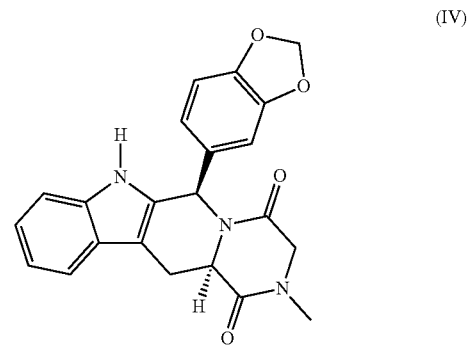 [SMILES: CN1CC(=O)N2[C@H](c3ccc4c(c3)OCO4)c3[nH]c4ccccc4c3C[C@@H]2C1=O]

(IV)

Other suitable PDE5 inhibitors of Formula III that can be utilized in the methods of the present invention are disclosed in U.S. Pat. No. 6,140,329 to Daugen, which is hereby incorporated by reference in its entirety, and include, without limitation:

Cis-2,3,6,7,12,12a-hexahydro-2-(4-pyridylmethyl)-6-(3,4-methylenedioxyphenyl)-pyrazino[2',1':6,1]pyrido[3,4-b]indole-1,4-dione;

Cis-2,3,6,7,12,12a-hexahydro-6-(2,3-dihydrobenzo[b]furan5-yl)-2-methyl pyrazino[2',1':6,1]pyrido[3,4-b]indole-1,4-dione;

Cis-2,3,6,7,12,12a-hexahydro-6-(5-bromo-2-thienyl)-2-methyl pyrazino[2',1':6,1]pyrido[3,4-b]indole-1,4-dione;

Cis-2,3,6,7,12,12a-hexahydro-2-butyl-6-(4-methylphenyl)-pyrazino[2',1':6,1]pyrido[3,4-b]indole-1,4-dione;

(6R,12aR)-2,3,6,7,12,12a-Hexahydro-2-isopropyl-6-(3,4-methylenedioxyphenyl)-pyrazino[2',1':6,1]pyrido[3,4-b]indole-1,4-dione;

(6R,12aR)-2,3,6,7,12,12a-Hexahydro-2-cyclopentyl-6-(3,4-methylenedioxyphenyl)-pyrazino[2',1':6,1]pyrido[3,4-b]indole-1,4-dione;

(6R,12aR)-2,3,6,7,12,12a-Hexahydro-2-cyclopropylmethyl-6-(4-methoxyphenyl)-pyrazino[2',1':6,1]pyrido[3,4-b]indole-1,4-dione;

(6R,12aR)-2,3,6,7,12,12a-Hexahydro-6-(3-chloro-4-methoxyphenyl)-2-methyl-pyrazino[2',1':6,1]pyrido[3,4-b]indole-1,4-dione;

(6R,12aR)-2,3,6,7,12,12a-Hexahydro-2-methyl-6-(3,4-methylenedioxyphenyl)-pyrazino[2',1':6,1]pyrido[3,4-b]indole-1,4-dione;

(6R,12aR)-2,3,6,7,12,12a-Hexahydro-6-(3,4-methylenedioxyphenyl)-pyrazino[2',1':6,1]pyrido[3,4-b]indole-1,4-dione;

(5aR,12R,14aS)-1,2,3,5,6,11,12,14a-Octahydro-12-(3,4-methylenedioxyphenyl)-pyrrolo[1",2":4',5']pyrazino[2',1':6,1]pyrido[3,4-b]indole-5-1,4-dione;

Cis-2,3,6,7,12,12a-hexahydro-2-cyclopropyl-6-(3,4-methylenedioxyphenyl)-pyrazino[2',1':6,1]pyrido[3,4-b]indole-1,4-dione;

(3S,6R,12aR)-2,3,6,7,12,12a-hexahydro-3-methyl-6-(3,4-methylenedioxyphenyl)-pyrazino[2',1':6,1]pyrido[3,4-b]indole-1,4-dione;

(6R,12aR)-2,3,6,7,12,12a-hexahydro-2-methyl-6-(3,4-methylenedioxyphenyl)-pyrazino[2',1':6,1]pyrido[3,4-b]indole-1,4-dione; and (3S,6R,12aR)-2,3,6,7,12,12a-hexahydro-2,3-dimethyl-6-(3,4-methylenedioxyphenyl)-pyrazino[2',1':6,1]pyrido[3,4-b]indole-1,4-dione and physiologically acceptable salts and solvates (e.g. hydrates) thereof.

In another embodiment of the present invention, the PDE-5 inhibitor comprises any one of the 2-phenyl-substituted imidazotriazinones disclosed in U.S Patent Application Publication No. 2006/0189615 to Niewohner et al., which is hereby incorporated by reference in its entirety. An exemplary 2-phenyl-substituted imidazotriazinone is vardenafil (available under the tradename Levitra® from Bayer Pharmaceuticals Corp.; Pittsburgh, Pa.) which comprises the formula of Formula V

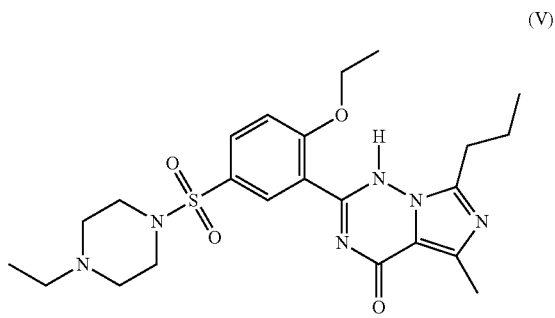 [SMILES: CCCc1nc(C)c2c(=O)nc(-c3cc(S(=O)(=O)N4CCN(CC)CC4)ccc3OCC)[nH]n12]

(V)

A suitable PDE5 inhibitor may be administered to the tissue graft at various time points. For example, the PDE5 inhibitor may be administered prior to removal of the tissue graft from the donor subject, after removal of the tissue graft from the donor subject, but prior to transfer to the recipient site, concurrently with implanting the tissue graft into a recipient site of the same or a different subject, and/or after implantation of the tissue graft into a recipient site of the same or a different subject.

In one embodiment of the present invention, the PDE5 inhibitor is administered to the tissue graft prior to harvesting the tissue. Suitable PDE5 inhibitors are described supra. In accordance with this embodiment of the invention, the PDE5 inhibitor can be administered between 1-24 hours prior to harvesting the tissue. In one embodiment of the present invention, the PDE5 inhibitor is administered 5-60 minutes prior to harvesting the tissue. In another embodiment of the present invention, the PDE5 inhibitor is administered between 10-45 minutes prior to harvesting the tissue. In another embodiment of the present invention, the PDE5 inhibitor is administered between 15-30 minutes prior to harvesting the tissue. The PDE5 inhibitor can be administered simultaneously with or subsequent to the administration of local anesthesia or tumescent fluid. Administration of the PDE5 inhibitor to the tissue prior to harvesting is preferably carried out using subcutaneous or intramuscular injection, although one of skill in the art readily appreciates that other routes of injection may also be suitable depending on the type of graft. Preferably administration is not systemic administration.

In another embodiment of the present invention, the PDE5 inhibitor is administered after harvesting the tissue graft from its donor site and prior to implantation into the recipient site. In accordance with this embodiment, the harvested or explanted tissue is maintained under conditions suitable to ensure viability, i.e., in a medium providing appropriate nutrients in the presence of oxygen/carbon dioxide at the appropriate temperature (e.g., standard tissue culture conditions of 37° C., 5% $CO_2$). While the harvested tissue can be maintained ex vivo for an extended period of time (e.g., hours, days, weeks), it is preferable to minimize the amount of time the harvested tissue is maintained ex vivo. The PDE5 inhibitor can be administered to the harvested tissue ex vivo 1-24 hours prior to transfer of the tissue to the recipient site. In one embodiment of the present invention, the PDE5 inhibitor is administered to the harvested tissue ex vivo 5-60 minutes prior to transfer to the recipient site. In another embodiment, the PDE5 inhibitor is administered to the harvested tissue ex vivo 10-45 minutes prior to transfer to the recipient site. In another embodiment, the PDE5 inhibitor is administered to the harvested tissue ex vivo 15-30 minutes prior to transfer of the tissue to the recipient site. The PDE5 inhibitor can be administered to the tissue ex vivo by injection. Alternatively, the PDE5 inhibitor can be added to the tissue media maintaining the explanted tissue graft to achieve exposure of the tissue to the PDE5 inhibitor prior to transfer.

The proper dosage of PDE5 inhibitor to the tissue graft free flap will vary depending on a number of variables, e.g., volume of tissue to be treated, incubation period, type of tissue being treated, route of administration etc., as can be appreciated by one of skill in the art. Generally, a suitable dosage of the PDE5 inhibitor will range between 1-1000 nM.

Another aspect of the present invention relates to an isolated tissue graft treated with a phosphodiesterase type-5 (PDE5) inhibitor. As described above, the explanted graft tissue can be maintained ex vivo after PDE5 inhibitor administration under conditions suitable for tissue survival. Suitable bioreactors and conditions for maintaining tissue grafts ex vivo are disclosed in U.S. Patent Application Publication No. 20040247567 to Gurtner et al., which is hereby incorporated by reference in its entirety.

Another aspect of the present invention relates to a method of microvascular free flap transfer. This method involves administering a phosphodiesterase type-5 (PDE5) inhibitor to a microvascular free flap to produce a treated microvascular free flap, and implanting the treated microvascular free flap into a recipient site of a host subject after said administering.

As used herein, a "microvascular free flap" refers to a tissue graft that comprises its own microvascular bed or intact microcirculatory network. Grossly, a microvascular free flap consists of large muscular arteries, leading to capacitance arterioles, endothelial lined capillaries, venules, veins and all of the phenotypically distinct cells within them (Siemionow et al., "Microcirculatory Hemodynamics During the Acute Phase of Free Vascularized Muscle Allograft," *Ann. Plast. Surg.* 41: 275-82 (1998), Carroll et al., "Ischemia/Reperfusion Injury in Microvascular Surgery," *Head Neck.* 22: 700-13 (2002), which are hereby incorporated by reference in their entirety). Importantly, in the native state, the free flap contains all of these cell types in a functional and precisely ordered three-dimensional configuration. As used herein, a microvascular free flap is not a whole organ.

In contrast to a tissue graft, which relies on the recipient site for vascularization, a microvascular free flap comprises an intact blood supply and vasculature which it brings with it to the recipient site. The blood supply of the free flap is reconstituted using microsurgery techniques to anastomose the afferent artery and efferent vein of the free flap to a recipient artery and vein at the transfer site. Like tissue grafts, microvascular free flap transfer is routinely performed for reconstructive as well as cosmetic purposes.

Suitable microvascular free flap tissues for use in accordance with the methods of the present invention include, without limitation, cutaneous flaps (flaps consisting of skin and subcutaneous tissue supplied by a direct cutaneous artery), fasciocutaneous flaps (flaps consisting of fascia, subcutaneous tissue, and skin supplied by septocutaneous perforator), myocutaneous flaps (flaps consisting of skin, subcutaneous tissue, and muscle), bone flaps, muscle flaps, nerve flaps, fascia flaps, intestine flaps, and periosteum flaps. The flaps of the present invention can also comprise a composite tissue flap, e.g., a osteocutaneous flap composed of bone and skin, a musculocutaneous flap composed of muscle and skin, a neurovascular flap, or a flap composed of adipose tissue and skin, fascia and muscle, or other such combination known to normally be present in the vertebrate body According to the methods of the invention, a microvascular free flap tissue may be harvested by conventional surgical methods known in the art (see e.g., Petry et al., "The Anatomy of the Epigastric Flap in Experimental Rat," *Plast. Reconstr. Surg.* 74: 410-13 (1984); Blackwell et al., "Reconstruction of Massive Defects in the Head and Neck: The Role of Simultaneous Distant and Regional Flaps," *Head Neck* 19: 620-28 (1997), which are hereby incorporated by reference in their entirety).

In accordance with this aspect of the present invention, the PDE5 inhibitor is administered to the microvascular free flap prior to transfer to its recipient site via vascular perfusion. Preferably, the PDE5 inhibitor is administered after flap harvest, but prior to transfer, i.e., while the flap is ex vivo. The flap can be maintained ex vivo using methods well-known in the art (see e.g., U.S. Patent Application Publication No. 20040247567 to Gurtner et al., which is hereby incorporated by reference in its entirety). The tissue is preferably perfused, e.g., the tissue can be wrapped in gauze, a catheter can be placed in a blood vessel associated with the tissue and secured with a suture, and the tissue perfused or infused with physiological saline. In one embodiment, the perfusion is conducted at a cold temperature (for cold ischemia). In other embodiments, perfusion is conducted at room temperature or body temperature. Preferably, the tissue is perfused ex vivo through a catheter at a constant perfusion pressure to flush out blood from the flap vessels. Preferably, the infusions are given at physiologic pressures (80-200 mm Hg), since high pressures cause excessive tissue damage, leading to necrosis of all or part of the flap. In one embodiment, a continuous microperfusion system is employed, such as the one described by Milas et al. "Isolated Limb Perfusion in the Sarcoma-Bearing Rat: A Novel Preclinical Gene Delivery System," *Clin. Cancer Res.* 3(12-1): 2197-2203 (1997), which is hereby incorporated by reference in its entirety. In other embodiments, an explanted flap can be maintained for a prolonged period of time ex vivo using a bioreactor as described in U.S. Patent Application Publication No. 20040247567 to Gurtner, which is hereby incorporated by reference in its entirety.

The proper dosage of PDE5 inhibitor to the tissue graft free flap will vary depending on a number of variables, e.g., volume of tissue to be treated, incubation period, type of tissue being treated, route of administration etc., as can be appreciated by one of skill in the art. Generally, a suitable dosage of the PDE5 inhibitor will range between 1-1000 nM.

Another aspect of the present invention relates to an isolated microvascular free flap treated with a phosphodiesterase type-5 (PDE5) inhibitor. As described above, the explanted microvascular free flap can be maintained ex vivo after PDE5 inhibitor administration under conditions suitable for promoting flap survival.

EXAMPLES

The examples below are intended to exemplify the practice of the present invention but are by no means intended to limit the scope thereof.

Example 1

Pretreatment of Donor Tissue with Sildenafil Improves Graft Take, Maintains Graft Volume, and Prolongs Survival To examine the effect of PDE5 inhibitor pretreatment of donor graft tissue on graft take and survival, transfer of syngeneic fat between Tie2/LacZ mice (donor) and wild type FVB mice (recipient) was performed. A schematic representation of the protocol is depicted in FIG. 1A. Since the transgenic mice express the lacZ gene in their blood vessels, donor and recipient vasculature can be independently visualized and assessed based on the presence or absence of lacZ gene expression.

Prior to harvesting the inguinal fat pads from 6-12 week old transgenic FVB Tie2/LacZ mice, the pads were infiltrated with small volumes of PBS (control) and 35 nM sildenafil citrate in PBS and allowed to dwell for 15-20 minutes. The pads were harvested, washed in PBS, and finely minced to simulate conditions of human harvest. The minced fat was centrifuged at 3000 rpm for 3 minutes and the aqueous and oil layers removed leaving the adipose layer for injection. The dorsum of syngeneic wildtype FVB mice was used as the recipient bed for the processed lipoaspirate, as previously described (Sultan et al., "Human Fat Grafting Alleviates Radiation Skin Damage in a Murine Model," *Plast Reconstr Surg* 128:363-72 (2011) and Thanik et al., "A Murine Model for Studying Diffusely Injected Human Fat," *Plast Reconstr Surg* 124:74-81 (2009), which are hereby incorporated by reference in their entirety). Autologous fat was infiltrated using a blunt tip cannula through a 2-mm caudal midline incision. The infiltration cannula was advanced and withdrawn in a fan like pattern in the dorsal subdermal plane of the mouse, to maintain an even layer over the entire dorsal surface.

Figure 2:
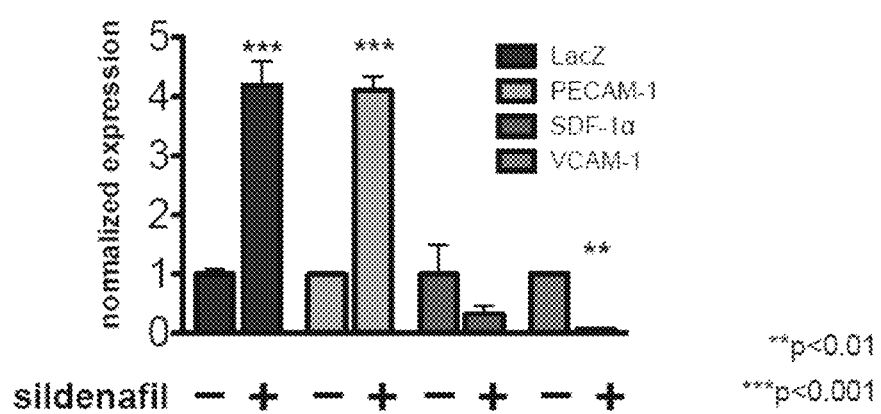
FIG. 2 is a graph showing endothelial cell gene expression in PDE5 inhibitor (i.e., sildenafil) treated or saline treated explanted grafts by quantitative PCR (qPCR).

PDE-5 inhibition prior to tissue harvest had a profound impact on fat graft survival following re-implantation. Quantitative PCR analysis of 2-day old explanted grafts demonstrated that sildenafil-based treatment improved donor-derived endothelial cell function/viability as indicated by increased LacZ and PECAM-1 expression (FIG. 2). In addition, sildenafil pre-treatment decreased expression of the inflammatory genes SDF-1α and VCAM (FIG. 2) in the explanted tissue.

Figure 3A:
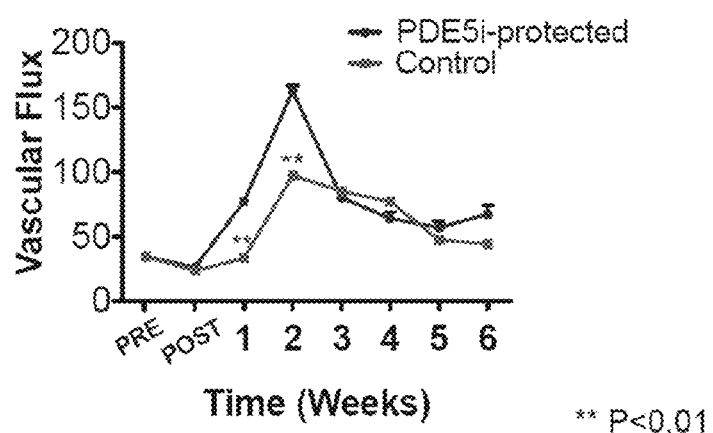
FIGS. 3A-3B show enhanced vascular flux in explanted grafts following treatment with sildenafil.
Figure 3B:
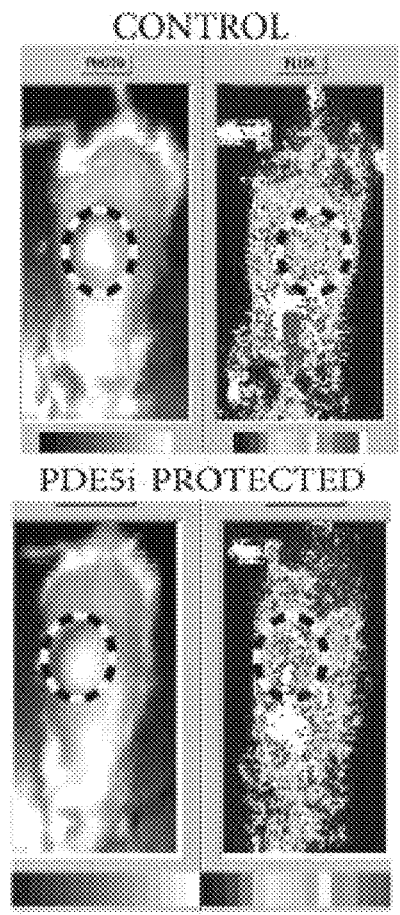
Figures 4A, 4B:
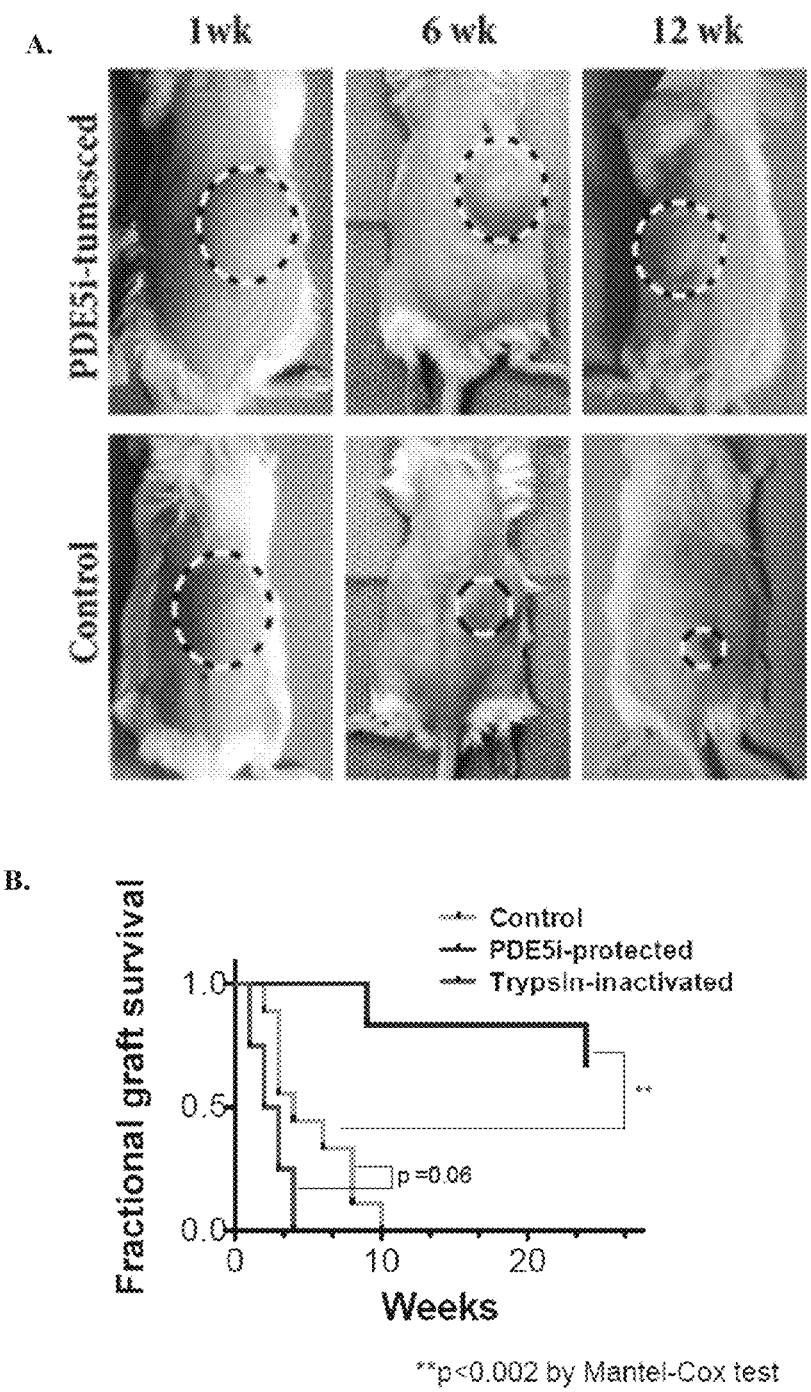
FIGS. 4A-4B show increased graft survival following treatment with sildenafil.

Pretreatment of the tissue graft with sildenafil also promoted faster restoration of blood flow within the grafted tissues in the first two weeks following transplantation as shown by quantitative measurement of vascular flux (FIGS. 3A-3B). Specifically, significant improvement in revascularization within the core of the sildenafil-treated graft as compared to control was observed at 1 and 2 weeks post grafting (FIGS. 3A-3B). Compared to saline treated grafts, which are reabsorbed quickly over the course of 12 weeks after transfer (FIG. 4A; bottom panel), the sildenafil treated graft maintained virtually all of its volume over time (FIG. 4A; top panel). The graft survival analysis of FIG. 4B shows that sildenafil treated grafts survive significantly longer than saline-treated control grafts and devascularized donor grafts ("trypsin-inactivated").

Figure 5A:
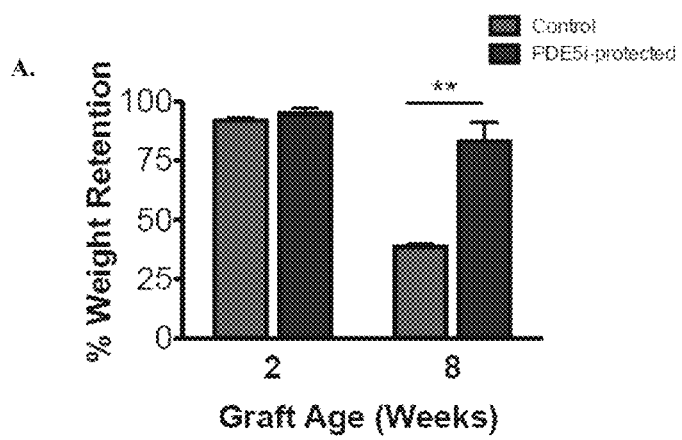
FIGS. 5A-5B show enhanced graft retention following treatment with sildenafil.
Figure 5B:
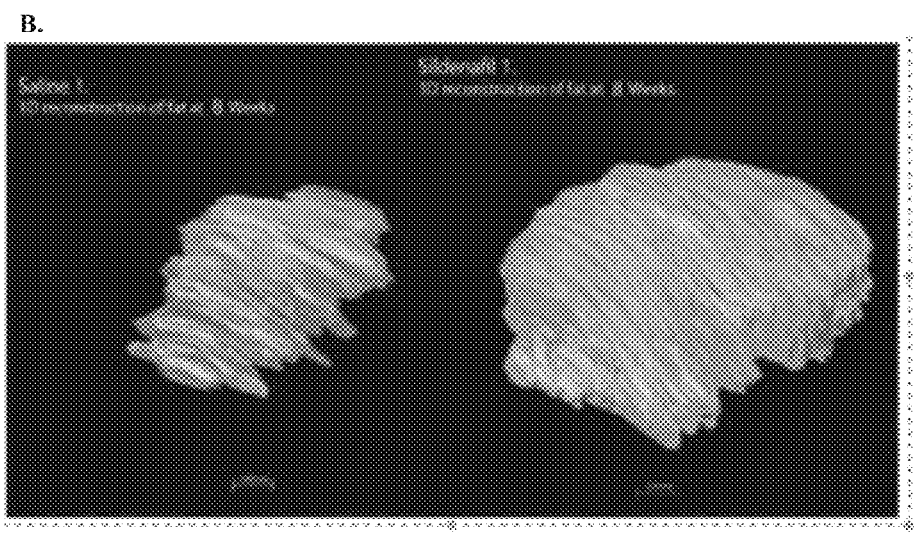

Finally, the sildenafil-treated grafts demonstrate >2-fold enhanced graft retention compared to saline treated grafts as indicated by the percent graft weight retention measured at 8 weeks post transplant (FIGS. 5A-5B). FIG. 5A is a graph showing graft weight retention of explanted grafts at 2 and 8 weeks post grafting. FIG. 5B is a volumetric analysis of control (left) and sildenafil treated (right) grafts via an in situ 3-D ultrasound rendering at 8 weeks post grafting.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of increasing the survival of an autologous fat tissue graft, said method comprising:
   administering, subcutaneously, a phosphodiesterase type-5 (PDE5) inhibitor to a site on subject, said site comprising a fat depot suitable for use as an autologous fat tissue graft;
   harvesting an autologous fat tissue graft from the site of the subject after said administering; and
   implanting the harvested autologous fat tissue graft into the subject, wherein said implanted autologous fat tissue graft survives longer after said implanting than an autologous fat tissue graft harvested from a site that was not administered a PDE5 inhibitor.

2. The method of claim 1, wherein the PDE5 inhibitor comprises Formula I:

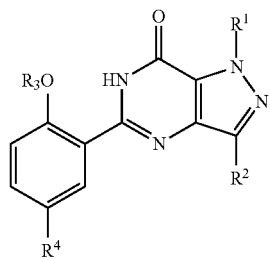

(I)

wherein
$R^1$ is H; $C_1$-$C_3$ alkyl; $C_1$-$C_3$ perfluoroalkyl; or $C_3$-$C_5$ cycloalkyl;
$R^2$ is H; $C_1$-$C_6$ alkyl optionally substituted with $C_3$-$C_6$ cycloalkyl; $C_1$-$C_3$ perfluoroalkyl; or $C_3$-$C_6$ cycloalkyl;
$R^3$ is $C_1$-$C_6$ alkyl optionally substituted with $C_3$-$C_6$ cycloalkyl; $C_1$-$C_6$ perfluoroalkyl; $C_3$-$C_5$ cycloalkyl; $C_3$-$C_6$ alkenyl; or $C_3$-$C_6$ alkynyl;
$R^4$ is $C_1$-$C_4$ alkyl optionally substituted with OH, $NR^5R^6$, CN, $CONR^5R^6$ or $CO_2R^7$; $C_2$-$C_4$ alkenyl optionally substituted with CN, $CONR^5R^6$ or $CO_2R^7$; $C_2$-$C_4$ alkanoyl optionally substituted with $NR^5R^6$; (hydroxy)$C_2$-$C_4$ alkyl optionally substituted with $NR^5R^6$; ($C_2$-$C_3$ alkoxy)$C_1$-$C_2$ alkyl optionally substituted with OH or $NR^5R^6$; $CONR^5R^6$; $CO_2R^7$; halo; $NR^5R^6$; $NHSO_2NR^5R^6$; $NHSO_2R^8$; $SO_2NR^9R^{10}$; or phenyl, pyridyl, pyrimidinyl, imidazolyl, oxazolyl, thiazolyl, thienyl or triazolyl any of which is optionally substituted with methyl;
$R^5$ and $R^6$ are each independently H or $C_1$-$C_4$ alkyl, or together with the nitrogen atom to which they are attached form a pyrrolidinyl, piperidino, morpholino, 4-N($R^{11}$)-piperazinyl or imidazolyl group wherein said group is optionally substituted with methyl or OH;
$R^7$ is H or $C_1$-$C_4$ alkyl;
$R^8$ is $C_1$-$C_3$ alkyl optionally substituted with $NR^5R^6$;
$R^9$ and $R^{10}$ together with the nitrogen atom to which they are attached form a pyrrolidinyl, piperidino, morpholino or 4-N($R^{12}$)-piperazinyl group wherein said group is optionally substituted with $C_1$-$C_4$ alkyl, $C_1$-$C_3$ alkoxy, $NR^{13}R^{14}$ or $CONR^{13}R^{14}$;
$R^{11}$ is H; $C_1$-$C_3$ alkyl optionally substituted with phenyl; (hydroxy)$C_2$-$C_3$ alkyl; or $C_1$-$C_4$ alkanoyl;
$R^{12}$ is H; $C_1$-$C_6$ alkyl; ($C_1$-$C_3$ alkoxy)$C_2$-$C_6$ alkyl; (hydroxy)$C_2$-$C_6$ alkyl; ($R^{13}R^{14}$N)$C_2$-$C_6$ alkyl; ($R^{13}R^{14}$NOC)$C_1$-$C_6$ alkyl; $CONR^{13}R^{14}$; $CSNR^{13}R^{14}$; or $C(NH)NR^{13}R^{14}$; and $R^{13}$ and $R^{14}$ are each independently H; $C_1$-$C_4$ alkyl; ($C_1$-$C_3$ alkoxy)$C_2$-$C_4$ alkyl; or (hydroxy)$C_2$-$C_4$ alkyl;
or a pharmaceutically acceptable salt thereof.

3. The method of claim 2, wherein the PDE-5 inhibitor comprises the formula of Formula II

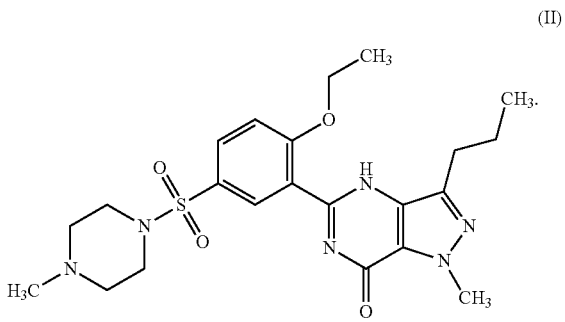 [SMILES: CCCc1nn(C)c2c(=O)nc(-c3cc(S(=O)(=O)N4CCN(C)CC4)ccc3OCC)[nH]c12]

(II)

4. The method of claim 3, wherein the PDE-5 inhibitor comprises 5-{2-Ethoxy-5-[(4-methyl-1-piperazinyl)sulfonyl]phenyl}-1-methyl-3-propyl-1,4-dihydro-7H-pyrazolo[4,3-d]pyrimidin-7-one 2-hydroxy-1,2,3-propanetricarboxylate (1:1).

5. The method of claim 1, wherein the PDE5 inhibitor comprises Formula III:

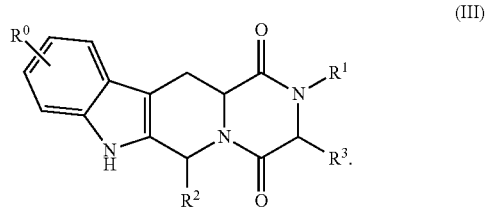

(III)

and salts and solvates thereof, in which:
$R^0$ represents hydrogen, halogen or $C_1$-$C_6$ alkyl;
$R^1$ represents hydrogen, $C_1$-$C_6$ alkyl, $C_2$-$C_6$ alkenyl, $C_2$-$C_6$ alkynyl, halo$C_1$-$C_6$ alkyl, $C_3$-$C_8$cycloalkyl, $C_3$-$C_8$cycloalkyl-$C_1$-$C_3$ alkyl, aryl $C_1C_3$alkyl or heteroaryl C-$C_3$alkyl;
$R^2$ represents an optionally substituted mono-cyclic aromatic ring selected from benzene, thiophene, furan and pyridine or an optionally substituted bicyclic ring

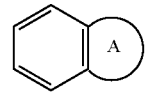

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and
$R^3$ represents hydrogen or $C_1$-$C_3$alkyl, or $R^1$ and $R^3$ together represent a 3- or 4-membered alkyl or alkenyl chain.

6. The method of claim 5, wherein the PDE-5 inhibitor comprises a formula of Formula IV
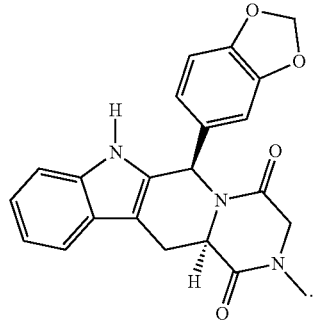
(IV)
7. The method of claim 1, wherein the PDE-5 inhibitor comprises a 2-phenyl-substituted imidazotriazinone.
8. The method of claim 7, wherein the PDE-5 inhibitor comprises a formula of Formula V
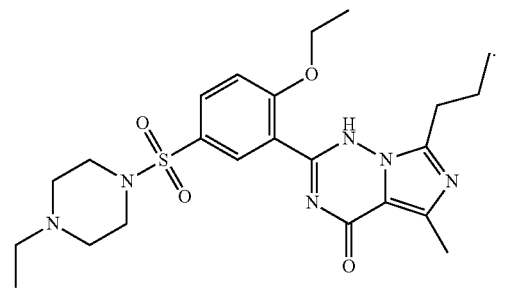
(V)
* * * * *